United States Patent
Malachowski

(10) Patent No.: US 6,589,792 B1
(45) Date of Patent: *Jul. 8, 2003

(54) METHOD AND APPARATUS FOR FLOW CYTOMETRY

(75) Inventor: George C. Malachowski, Fort Collins, CO (US)

(73) Assignee: DakoCytomation Denmark A/S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/623,188

(22) PCT Filed: Feb. 26, 1999

(86) PCT No.: PCT/US99/04183

§ 371 (c)(1),
(2), (4) Date: Aug. 25, 2000

(87) PCT Pub. No.: WO99/44037

PCT Pub. Date: Sep. 2, 1999

Related U.S. Application Data

(63) Continuation-in-part of application No. 09/032,733, filed on Feb. 27, 1998, now Pat. No. 6,248,590.

(51) Int. Cl.$^7$ ............................................... G01N 33/48
(52) U.S. Cl. ........................ 436/63; 436/164; 422/73; 422/82.05; 209/3.2; 209/552; 209/576; 209/127.4; 382/133
(58) Field of Search ...................... 436/63, 164; 422/73, 422/82.05; 356/72, 73; 250/461.2; 209/3.1, 3.2, 3.3, 571, 576–579, 552, 906, 127.4; 382/133

(56) References Cited

U.S. PATENT DOCUMENTS

| | | | |
|---|---|---|---|
| 3,299,354 A | 1/1967 | Hogg | 207/582 |
| 3,661,460 A | 5/1972 | Elking et al. | 356/36 |
| 3,710,933 A | 1/1973 | Fulwyler et al. | 209/3 |
| 3,761,941 A | 9/1973 | Robertson | 346/1 |
| 3,810,010 A | 5/1974 | Thom | 324/71 |
| 3,826,364 A | 7/1974 | Bonner et al. | 209/3 |
| 3,833,796 A | 9/1974 | Fetner et al. | 236/151.3 |
| 3,960,449 A | 6/1976 | Carleton et al. | 356/103 |
| 3,963,606 A | 6/1976 | Hogg | 209/3 |

(List continued on next page.)

FOREIGN PATENT DOCUMENTS

DE   19549015   3/1997   ............... 21/85

(List continued on next page.)

OTHER PUBLICATIONS

Garner, D.L., et al., "Quantification of the X–and Y–Chromosome–Bearing Spermatozoa of Domestic Animals by Flow Cytometry", Biology of Reproduction 28, pp. 312–321 (1983).

(List continued on next page.)

Primary Examiner—Maureen M. Wallenhorst
(74) Attorney, Agent, or Firm—Santangelo Law Offices, P.C.; Craig R. Miles

(57) ABSTRACT

A flow cytometer (20) capable of utilizing an imaging system including a sensor (88) to determine various properties of the flow cytometer (20). Importantly, the imaging allows for determination of a drop delay time (154). Other characteristics that can be determined include at least the width of the stream, pressure of the stream, effect of charged droplets on other droplets (44), trajectory of the stream, resonant frequency, wavelengths, change in position of droplet break-off point (150), and others. An automatic warning system (180) can be used to alert an operator of an anomaly during setup or during normal operation. Furthermore, a mechanical interrupter can be used to shield a sort result from contamination by an incorrectly functioning stream. The cytometer (20) also allows for the disablement of the sort, particularly the charging and deflection systems. In addition, a more accurate system for detecting the speed of the stream can be used. The imaging system including a sensor (88) can allow for the removal of background noise and the monitoring of a change in a stream characteristic.

47 Claims, 4 Drawing Sheets

U.S. PATENT DOCUMENTS

| | | | | |
|---|---|---|---|---|
| 3,973,196 A | 8/1976 | Hogg | | 324/71 |
| 4,014,611 A | 3/1977 | Simpson et al. | | 356/72 |
| 4,070,617 A | 1/1978 | Kachel et al. | | 324/71 |
| 4,162,282 A | 7/1979 | Fulwyler et al. | | 264/9 |
| 4,230,558 A | 10/1980 | Fulwyler | | 209/3.1 |
| 4,302,166 A | 11/1981 | Fulwyler et al. | | 425/6 |
| 4,317,520 A | 3/1982 | Lombardo et al. | | 209/3.1 |
| 4,318,480 A | 3/1982 | Lombardo et al. | | 209/3.1 |
| 4,318,481 A | 3/1982 | Lombardo et al. | | 209/3.1 |
| 4,318,482 A | 3/1982 | Barry et al. | | 209/3.1 |
| 4,318,483 A | 3/1982 | Lombardo et al. | | 209/3.1 |
| 4,325,483 A | 4/1982 | Lombardo et al. | | 209/3.1 |
| 4,341,471 A | 7/1982 | Hogg et al. | | 356/343 |
| 4,350,410 A | 9/1982 | Minott | | 350/170 |
| 4,361,400 A | 11/1982 | Gray et al. | | 356/23 |
| 4,395,676 A | 7/1983 | Hollinger et al. | | 324/71.4 |
| 4,400,764 A | 8/1983 | Kenyon | | 362/263 |
| 4,487,320 A | 12/1984 | Auer | | 209/3.1 |
| 4,498,766 A | 2/1985 | Unterleitner | | 356/73 |
| 4,515,274 A | 5/1985 | Hollinger et al. | | 209/3.1 |
| 4,523,809 A | 6/1985 | Taboada et al. | | 350/163 |
| 4,538,733 A | 9/1985 | Hoffman | | 209/3.1 |
| 4,598,408 A | 7/1986 | O'Keefe | | 372/94 |
| 4,600,302 A | 7/1986 | Sage, Jr. | | 356/39 |
| 4,631,483 A | 12/1986 | Proni et al. | | 324/71.4 |
| 4,673,288 A | 6/1987 | Thomas et al. | | 356/72 |
| 4,691,829 A | 9/1987 | Auer | | 209/3.1 |
| 4,702,598 A | 10/1987 | Böhmer | | 356/343 |
| 4,744,090 A | 5/1988 | Freiberg | | 372/94 |
| 4,758,729 A | 7/1988 | Monnin | | 250/560 |
| 4,794,086 A | 12/1988 | Kasper et al. | | 436/36 |
| 4,818,103 A | 4/1989 | Thomas et al. | | 356/72 |
| 4,831,385 A | 5/1989 | Archer et al. | | 346/1.1 |
| 4,845,025 A | 7/1989 | Lary et al. | | 435/2 |
| 4,942,305 A | 7/1990 | Sommer | | 250/574 |
| 4,981,580 A | 1/1991 | Auer | | 209/3.1 |
| 4,983,038 A | 1/1991 | Ohki et al. | | 356/246 |
| 5,005,981 A | 4/1991 | Schulte et al. | | 366/219 |
| 5,007,732 A | 4/1991 | Ohki et al. | | 356/73 |
| 5,030,002 A | 7/1991 | North, Jr. | | 356/73 |
| 5,079,959 A | 1/1992 | Miyake et al. | | 73/864.85 |
| 5,098,657 A | 3/1992 | Blackford et al. | | 422/73 |
| 5,101,978 A | 4/1992 | Marcus | | 209/3.1 |
| 5,127,729 A | 7/1992 | Oetliker et al. | | 356/317 |
| 5,144,224 A | 9/1992 | Larsen | | 324/71.4 |
| 5,150,313 A | 9/1992 | van den Engh et al. | | 364/569 |
| 5,159,397 A | 10/1992 | Kosaka et al. | | 356/73 |
| 5,159,403 A | 10/1992 | Kosaka | | 356/243 |
| 5,167,929 A | 12/1992 | Kimura et al. | | 422/67 |
| 5,180,065 A | 1/1993 | Touge et al. | | 209/577 |
| 5,182,617 A | 1/1993 | Yoneyama et al. | | 356/440 |
| 5,199,576 A | 4/1993 | Corio et al. | | 209/564 |
| 5,215,376 A | 6/1993 | Schulte et al. | | 366/348 |
| 5,247,339 A | 9/1993 | Ogino | | 356/73 |
| 5,259,593 A | 11/1993 | Orme et al. | | 266/78 |
| 5,260,764 A | 11/1993 | Fukuda et al. | | 356/73 |
| 5,298,967 A | 3/1994 | Wells | | 356/336 |
| 5,359,907 A | 11/1994 | Baker et al. | | 73/865.5 |
| 5,370,842 A | 12/1994 | Miyazaki et al. | | 422/82.06 |
| 5,412,466 A | 5/1995 | Ogino | | 356/246 |
| 5,452,054 A | 9/1995 | Dewa et al. | | 355/67 |
| 5,466,572 A | 11/1995 | Sasaki et al. | | 435/2 |
| 5,467,189 A | 11/1995 | Kreikebaum et al. | | 356/336 |
| 5,471,294 A | 11/1995 | Ogino | | 356/73 |
| 5,483,469 A | 1/1996 | Van den Engh et al. | | 364/555 |
| 5,558,998 A | 9/1996 | Hammond et al. | | 435/6 |
| 5,596,401 A | 1/1997 | Kusuzawa | | 356/23 |
| 5,601,235 A | 2/1997 | Booker et al. | | 239/4 |
| 5,602,039 A | 2/1997 | Van den Engh | | 436/164 |
| 5,602,349 A | 2/1997 | Van den Engh | | 73/864.85 |
| 5,641,457 A | 6/1997 | Van den Engh | | 422/82.01 |
| 5,643,796 A | 7/1997 | Van den Engh et al. | | 436/50 |
| 5,650,847 A | 7/1997 | Maltsev et al. | | 356/336 |
| 5,675,401 A | 10/1997 | Wangler et al. | | 355/67 |
| 5,700,692 A | 12/1997 | Sweet | | 436/50 |
| 5,707,808 A | 1/1998 | Roslaniec et al. | | 435/6 |
| 5,824,269 A | 10/1998 | Kosaka et al. | | 422/73 |
| 5,916,449 A | 6/1999 | Ellwart et al. | | 210/745 |
| 6,248,590 B1 * | 6/2001 | Malachowski | | 209/127.4 |
| 6,372,506 B1 * | 4/2002 | Norton | | 209/127.4 |

FOREIGN PATENT DOCUMENTS

| | | | | |
|---|---|---|---|---|
| EP | 0025296 A2 | 8/1980 | | G01N/15/07 |
| EP | 01690201 A2 | 3/1985 | | G01N/15/14 |
| EP | 0468100 A1 | 12/1990 | | G01N/15/14 |
| EP | 0781985 A2 | 7/1997 | | G01N/13/02 |
| FR | 2699678 A1 | 12/1992 | | G01N/21/64 |
| JP | 61139747 A | 6/1986 | | G01N/21/53 |
| JP | 61159135 A | 7/1986 | | G01N/21/17 |
| JP | 2024535 A | 1/1990 | | G01N/15/14 |
| JP | 4126064 A | 4/1992 | | A23P/1/08 |
| JP | 4126065 A | 4/1992 | | A23P/1/12 |
| JP | 4126066 A | 4/1992 | | C12M/1/02 |
| JP | 4126079 A | 4/1992 | | C12N/9/48 |
| JP | 4126080 A | 4/1992 | | C12N/9/90 |
| JP | 4126081 A | 4/1992 | | C12N/15/02 |
| SU | 1056008 | 11/1983 | | G01N/21/24 |
| SU | 1260778 A1 | 9/1986 | | G01N/21/64 |
| WO | WO99/44037 | 9/1999 | | |

OTHER PUBLICATIONS

Gottlinger, C., et al, "Operation of a Flow Cytometer", Flow Cytometry and Cell Sorting, pp. 7–23 (1982).

Johnson, L.A., "Sex Preselection by Flow Cytometric Separation of X and Y Chromosome–bearing Sperm based on DNA Difference: a Review", Reprod. Fertil. Dev., pp. 893–903 (1995).

McLeod, J. Eastman Kodak Company, Hawk–Eye Works, Rochester, NY, Journal of the Optical Society of America; vol. 44, No. 8, Sep. 1953, pp. 592–597.

Melamed, M.R., et al, "An Historical Review of the Development of Flow Cytometers and Sorters", A Review for Cytometers and Sorters, pp. 3–9, (1979).

Pinkel, D., "Flow Chambers and Sample Handling", Flow Cytometry: Instrumentation and Data Analysis, pp. 77–128 (1985).

Skogen–Hagenson, M.J., et al, "A High Efficiency Flow Cytometer", The Jouranl of Histochemistry and Cytochemistry, vol. 25, No. 7, pp. 784–789 (1977).

US Application 09/032,733, entitled "Method and Apparatus for Flow Cytometry", filed on Feb. 27,1998, 53 pages and 5 figures.

Van Dilla, M., "Overview of Flow Cytometry: Instrumentation and Data Analysis", Flow Cytometry: Instrumentation and Data Analysis, pp. 1–8 (1985).

* cited by examiner

METHOD AND APPARATUS FOR FLOW CYTOMETRY

This application is the United States National Stage of International Application No. PCT/US99/04183, filed Feb. 26, 1999, which is a continuation-in-part of U.S. patent application Ser. No. 09/032,733, filed Feb. 27, 1998, now U.S. Pat. No. 6,248,590, issued on Jun. 19, 2001, each hereby incorporated by reference.

I. TECHNICAL FIELD

This invention relates to a method and apparatus for the analyzation and sorting of particles, e.g., in a flow cytometer. In the field of flow cytometry it is common to establish a stream of sheath fluid with a stream of particles suspended in that sheath fluid. This stream can then be perturbed such that droplets form and the particles are contained in the droplets as they break-off from the end of a contiguous stream. The droplets can then be sorted as desired by detecting desired particles and establishing a charge on an individual droplet just before it breaks away from the contiguous part of the stream. The droplet containing the desired particle can then be deflected with an electric field into a collection container. As part of this process, it is optimal to know when a droplet containing a desired particle reaches the charging location such that that particular droplet can be charged while droplets charging as few neighboring droplets as necessary. This allows the droplet containing the desired particle and possibly a few droplets on either side of the droplet containing the particle—to be deflected into a separate container and sorted out of the stream.

As part of this process it has been necessary to set up a flow cytometer on a daily basis and to allow that flow cytometer to equilibrate to the environmental conditions where the flow cytometer is located. This takes approximately an hour to an hour and a half just for the process of equilibrating the flow cytometer. Then, typically another one-half hour is required to calibrate the drop delay timing of the flow cytometer after the equilibration period expires. Therefore, a full one to two hours is required on a daily basis just for setup of the flow cytometer. This is time that could be used for producing results from the flow cytometer rather than wasting it on setup time. Therefore, there is a desire for a flow cytometer that does not require this one to two hour setup time and that can be implemented quickly without the need for equilibration and calibration.

Another drawback to the present state of flow cytometry is the lack of an automatic means of compensating for change in one of the parameters of the flow cytometer—most importantly, the drop delay time. For example, it is currently necessary for a technician to monitor a sorting flow cytometer during the process of sorting. The technician must remain in the room while the sort is being performed in case a catastrophic failure of the flow cytometer would occur. In such a case, the technician could then, as quickly as possible, interrupt the sort and prevent any gathered sample of cells, for example, from being contaminated during a catastrophic failure. This might occur, for example, if a nozzle becomes clogged and the stream is angled away from the nozzle tip toward one of the sample collectors. Even with a technician in the room watching the sort take place, it would still require possibly two to three seconds for the flow cytometer to be stopped. In the case of some types of sorts, however, even this two to three second period would be too long to save the sort. Therefore, the process would have to be re-started and performed again. This can be quite frustrating—particularly if the sort had been near completion.

Furthermore, currently no warning system appears to exist when a parameter of the flow cytometer is set up in an incorrect manner. For example, if an incorrect nozzle size has been put on the flow cytometer, no manufacturer appears to be issuing a warning that can be used to alert the technician that the wrong nozzle size is attached. Therefore, this can result in unnecessary time on the part of the technician in trying to determine the problem with the setup of the flow cytometer.

Another drawback to the present state of the art in flow cytometry is the inability to determine a drop delay time for a particle to the degree of precision desired. Presently, one method that is used is to establish the stream and strobe the stream with a light source such that the stream can then be viewed on a monitor to see if the droplet break-off point of the stream changes position. If the break-off point shifts, then the stream can be re-calibrated to set the drop delay time for a particle. This is deceptive however, because a change in wavelength of the stream might occur without a resulting change in the droplet break-off point. Consequently, the drop delay time for a particle would change—as the change in wavelength would indicate a change in speed of the fluid flow. However, this would go unnoticed by a technician who was relying on the droplet break-off point position. It also assumes that the hydrodynamics of the stream are constant once the stream leaves the nozzle of the flow cytometer and thus, assumes the velocity of the stream remains constant.

II. BACKGROUND

Prior work in the field of flow cytometry apparently has been unsuccessful in solving these problems. Furthermore, they have focused on maintaining the droplet break off point—rather than appreciating the ability to determine a drop delay time for a particle. For example, U.S. Pat. No. 4,691,829 to Robert E. Auer tried to utilize a laser beam aimed at the stream above the droplet break-off point. Based on refractive properties of the stream, it was then attempted to detect changes in the surface of the stream. A change in the undulations of the surface could then be used to determine when the break-off point had shifted. However, this method did not actually determine a drop delay time for a particle detected in the stream. It merely tried to maintain the droplet break-off point at the same position. Furthermore, it required very sensitive equipment to detect the change in the undulation of the surface and has apparently since the patent issued in 1987 never been made to work in a commercial product.

An earlier attempt to try to control the droplet break-off point can be seen in U.S. Pat. No. 3,761,941. In that patent, a test sample was run through the cytometer to try to detect a charge on a droplet. A theoretical charge that was expected to have been applied to the droplet was then compared to the actual charge on the droplet. The amplitude of the drop stimulating disturbance was then adjusted until the actual charge approached the theoretical charge. In this manner, the stream could be adjusted to the correct point for charging purposes.

In 1982, U.S. Pat. No. 4,361,400 discussed the use of a television monitor to view the breakoff point of a cytometer. However, it also required the operator to manually adjust the settings of the cytometer based on the viewed breakoff point. Therefore, equilibration of the cytometer was still likely a one and a half hour procedure if this method were used.

In 1997, U.S. Pat. No. 5,700,692 discussed the use of a camera/monitor system to allow a user to adjust the distance between droplets in a cytometer. However, it did not appreciate the ability of a monitoring system to determine a wealth of other characteristics of a stream and thereby automatically provide feedback to the flow cytometer. Instead, it focused on determining a center of mass of droplets and assumed a constant velocity of the fluid stream. In focusing on the center of mass of droplets, it apparently completely overlooked important information that could be determined from the stream—including an automatic regulation of a drop delay time.

Consequently, there is still a need for a flow cytometer that can monitor a stream of the cytometer and detect a drop delay time based on the specific characteristics of the stream at a specific point in time. Rather than relying on an expected steady state condition, such as a constant velocity of the stream, there is a need for a cytometer that can determine the drop delay time under the specific conditions of the stream for a particular particle that is about to be sorted. Furthermore, there is a need for a flow cytometer that can adjust the drop delay time at the beginning of the day when the flow cytometer is still adjusting to environmental conditions such as room temperature. In this way, the flow cytometer can be used for useful sorts during the first one to two hours that were previously required for equilibration to environmental conditions and calibration of the flow cytometer, such as calibration of the drop delay time using a standard test sample. There is also still a need for a flow cytometer that can detect when a catastrophic event occurs that could result in the destruction of a nearly completed sort—for example a five to six hour sort that is contaminated when a nozzle becomes blocked and the stream is inadvertently diverted into the sample collection container. In addition, there is still a need for an automatic interrupter that can divert or block a stream or turn off the sorting aspect of the stream automatically upon the occurrence of an event such as a catastrophic failure. In this manner the collected sample could be protected in as fast a time as possible, especially faster than the two to three seconds that would be required if an operator were to do it by hand—as is apparently the case with current cytometers.

In addition, there is a need to understand the characteristics of the speed of the stream that is ejected by a flow cytometer—especially from the time that the stream is ejected from the flow cytometer through the point where a droplet is charged so that a charge can be applied at the droplet when the droplet reaches the charging location. In the past, it has been assumed that the speed was constant. However, as throughput is increased and particles become closer to one another in the stream, it is even more critical to be able to determine the speed of the stream drop delay time as accurately as possible; therefore, it is equally critical to understand the characteristics of the stream rather than simply estimate the stream as having a constant velocity.

III. DISCLOSURE OF INVENTION

The present invention provides a novel method of compensating for changes in a flow cytometer and accurately determining a drop delay time for a particular particle in the stream. A detected droplet can be charged based on a drop delay time that is computed based on a measurement of the speed of the fluid in the stream. Therefore, knowledge of the droplet charging location and the speed characteristics of the stream allows the cytometer to more accurately charge the droplet containing the particle at the droplet charging location.

In addition, other embodiments of the invention allow an image of the stream to be captured to determine information about the flow cytometer. For example, an image of the stream can be used to determine the width of the stream at a given point and correlate this to a nozzle size being used by the cytometer. In this fashion, it can be determined whether the correct nozzle size is being used. Other parameters can be determined in this fashion as well. For example, a velocity of the stream can be determined at various points along the stream. A velocity of the stream can be determined by measuring a wavelength of a surface wave on the stream and knowing the oscillation frequency that is being used by the mechanical device perturbing the stream in order to calculate the velocity of the stream at that point. Or, droplets occurring below the droplet break-off point can be imaged and a distance between the two droplets determined in order to determine the speed of the stream at the droplet break-off point.

Furthermore, an exponentially decaying model can be used to model the change in velocity of the stream below the nozzle exit point—particularly between the nozzle exit point and the droplet break-off point for the stream fluid. This model can then be used to determine a more exact drop delay time for a particle detected in the stream.

In addition, the image monitoring system can be used to image the droplet break-off point to determine a location of the droplet break-off point, as well as a change in position of the droplet break-off point. Furthermore, the system can be used to provide a feedback signal to the flow cytometer such that the droplet break-off point is re-established or maintained at the desired position.

Also, the image monitoring system can be used to determine the effect of a charged droplet on a successive droplet or droplets. This can be accomplished by monitoring the trajectory of a droplet in real time and charging the subsequent droplet with a slight charge that allows it to fall in line with other droplets that do not contain particles.

The imaging system can also be used in a similar manner to determine the most stable position of the stream for a given pressure and oscillation. In this manner the preferred resonant frequency for a stream can be selected and the resulting stream established in a stable position that will not require oscillating between positions.

The invention can also be used to warn an operator of the flow cytometer that an anomaly exists in the setup or operation of the flow cytometer. In this fashion, the cytometer can perform a self-test during setup as well as during operation. For example, a determination of the speed of the stream could be used to determine whether the correct hydraulic pressure is being used for the flow cytometer. Or, a warning can be issued to the operator inquiring whether a different nozzle size is intended based on a width of the stream, for example. Similarly, a shift in position of the stream could be used to determine if the nozzle has become clogged or whether some other anomaly exists with the cytometer. Furthermore, if the stream is detected to have disappeared completely, the cytometer could warn the operator that a catastrophic event that would damage the sort had occurred. These warnings might be issued to either a remote monitor, a paging device, alarm device, or even an e-mail message.

Furthermore, rather than simply issuing a warning to the operator, mechanical intervention can be utilized to automatically or manually divert the stream and prevent it from contaminating a gathered sample. This might be accomplished using either a gutter or deflector. Alternatively or concurrently, one embodiment of the invention allows the sort to be disabled, either manually or automatically, by disabling the charging of the stream and/or disabling the deflection force that typically deflects a charged particle.

The invention also utilizes imaging methods to remove electrical noise from the captured images. For example an image of the stream can be captured and outlined to establish a first background image of the stream and then used as a template for comparison of subsequent images of the stream. In this fashion, electrical noise can be removed on subsequent images and the outline of the images compared to see if there has been a change in a characteristic of the stream.

IV. BRIEF DESCRIPTION OF THE DRAWINGS

V. BEST MODE FOR CARRYING OUT THE INVENTION

Figure 1:
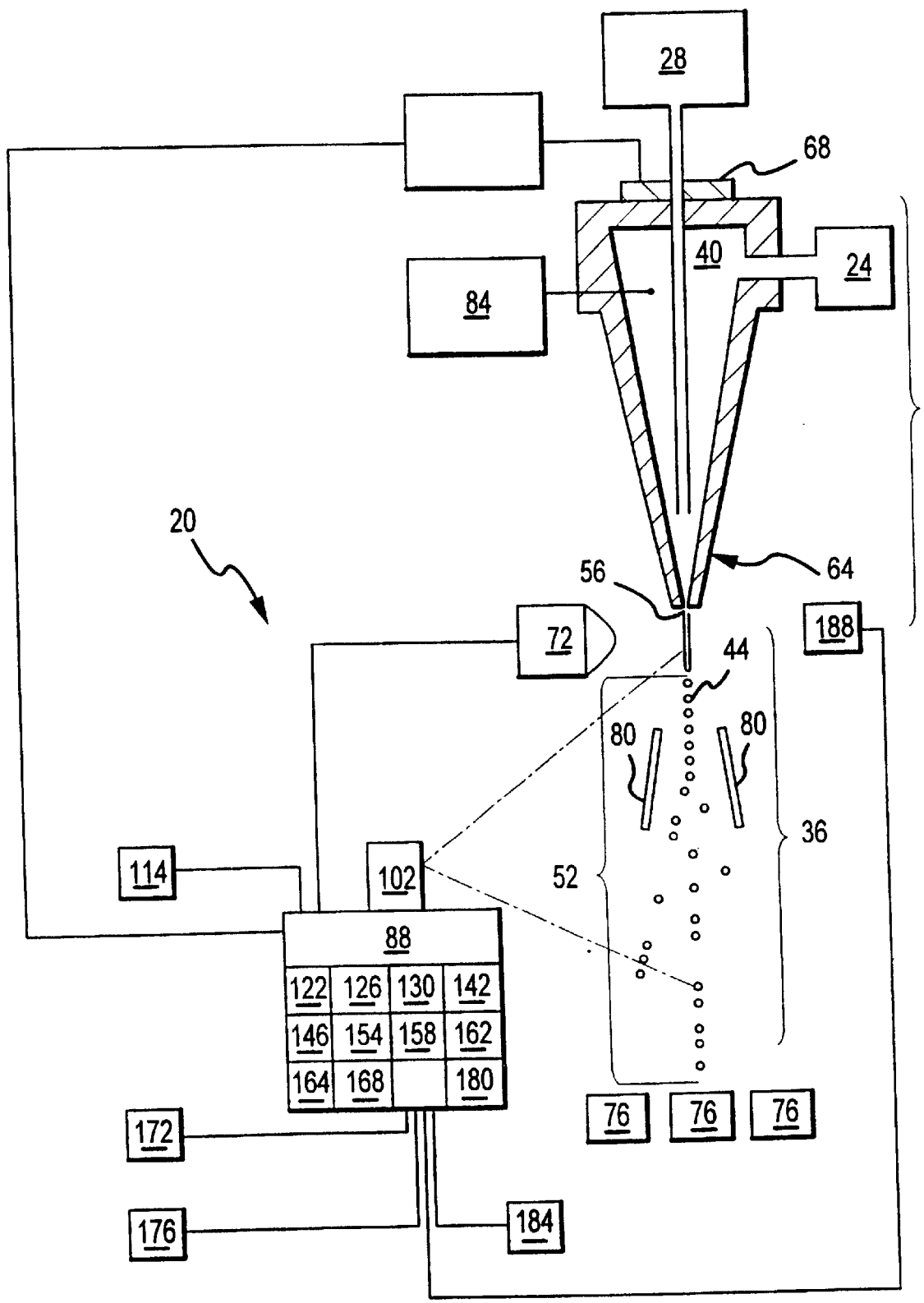
FIG. 1 is a schematic block diagram of an apparatus of one embodiment of the present invention.
Figure 2:
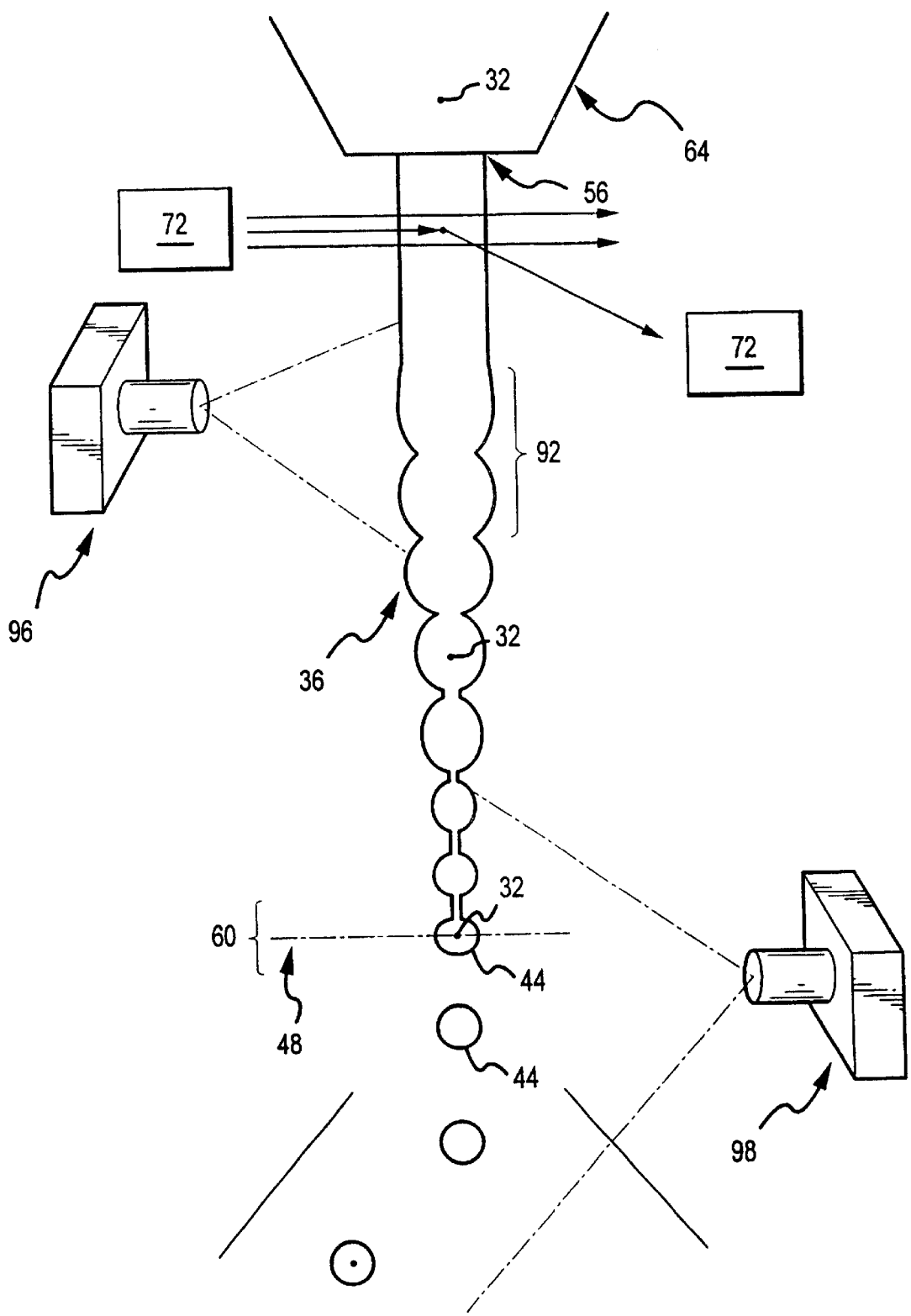
FIG. 2 is an alternative diagram of a closeup view of a flow cytometer stream.

Referring now to FIG. 1, a preferred embodiment of the invention can be seen in detail. The flow cytometer (20) can utilize a source of stream fluid (24) to supply stream fluid to establish a sheath of fluid in which particles (32) can be suspended. The source of particles (28) can insert the particles from time to time such that the particles become suspended in the stream fluid and are hydrodynamically focused in the stream. A stream (36) comprised of the stream fluid (40) and the particles (32) can then be established below the nozzle (64) of the flow cytometer. The stream can be established in a steady state condition such that droplets (44) are formed and break away from a contiguous part of the stream. When the stream is established in this steady state fashion, a stable break-off point (48) can be established. This stream can be strobed with a stroboscope to illuminate the stable stream. At the break-off point the stream breaks off into droplets with these droplets centered about the break-off point. The droplet break off point is the point in a stream where a droplet separates from the contiguous flow of the stream. For reference purposes, the center of the droplet will be considered the droplet break off point when it is necessary to define the point in such an exacting manner. Below the droplet break-off point (48) a free fall zone (52) can exist. This free fall zone embodies the area where the droplets move once they break away from the contiguous part of the stream. At the bottom of the nozzle (64) a stream exit point (56) is established. The exit point is the point in space where the stream emerges from the flow cytometer. For example, the exit point on a flow cytometer having a nozzle would exist where the stream exits from the nozzle. At this point the stream essentially emerges or is ejected from the flow cytometer. A droplet charging location (60) can exist at a point along the stream. This droplet charging location (60) can exist, for example, at the droplet break-off point (48) as seen in FIG. 2. As a possible alternative, a charging ring can be used and positioned below the droplet break-off point such that the individual droplets can be charged. An oscillator (68) as shown in FIG. 1, can be used to perturb the stream and to establish a steady state oscillation of the stream. It is preferred to use a piezoelectric crystal to accomplish this perturbation of the stream. The oscillator (68) may have an adjustable oscillation frequency that can be adjusted to perturb the stream at different frequencies such that droplets are created at different rates. Furthermore, it can be used in conjunction with the stream pressure to establish the rate of droplet formation.

A detector (72), such as a laser and receiver in combination, can be used as seen in FIG. 1 to monitor the stream for a particle. The detector can detect the particle in the stream as the particle passes through, for example, a coherent beam of light aimed at the stream by the detector. When the coherent beam of light intercepts a particle in the stream, fluorescence or scattered light rays can then be emitted or deflected, respectively, as shown in FIG. 2 to a receiver of the detector. Alternative methods of detection are also well understood by those of ordinary skill in the art.

As the droplets fall in the free fall zone, they can pass through a sorting force generator (80) such as electrostatic plates shown in FIG. 1. If the droplets have been charged with a positive or negative charge, an electric field established between these electrostatic plates will deflect the charged droplets such that the trajectory of the droplets is changed. As seen in FIG. 1, these droplets can then be deflected into a container (76) which acts as a sample collector. Similarly, those droplets that are neutrally charged can fall into the center container shown in FIG. 1 and droplets that are alternatively charged can fall into a third container. Furthermore, alternative techniques such as utilizing different quantities of charge can be used to accomplish an even greater deflection.

To accomplish the charging of the droplets a charging device (84) can be used to charge the stream fluid. Therefore, when a particle is detected and known to have reached the droplet break-off point, the stream can be charged such that when the droplet breaks away from the stream, it contains a net charge. A net charge should be understood to mean either a net positive, net negative, or even a neutral charge. Then, the charging device can be turned off or even configured to produce an opposite charge such that subsequent droplets which have been induced with a charge by the droplet containing a particle are counteractively charged back to the steady state charge of the stream—typically a neutral charge.

A sensor (88) can be used to accomplish many of.the techniques of the present invention. Initially, the sensor (88) can measure a property of the flow cytometer based on a captured image of the fluid stream. One such property that the sensor can measure is the speed of the stream at a point along the stream. Two points of particular interest are the speed of the stream at the area just below the exit point of the stream from the nozzle and at about the droplet break-off position of the stream.

The sensor (88) can be oriented to measure a wavelength (92) of the stream as shown in FIG. 2. Digital imaging routines can operate on the wave shape to measure the length of a standing wave, for example. Furthermore, the sensor can be oriented to measure a distance between droplets of the stream such that the distance and the oscillation frequency of the oscillator can be utilized to calculate the speed of the droplets at that point along the stream. The sensor (88) can utilize a camera (102) with a wide angle lens that captures a large portion of the stream or multiple cameras such as those seen in FIG. 2 where a camera (96) captures an image of the stream at an exit point of the stream and camera (98) captures an image at the droplet break-off point of the stream. In this fashion, camera (96) and camera (98) can serve as a first sensor and second sensor, respectively, for determining speeds at different points along the stream. The camera (102) as shown in FIG. 1, can capture an image (106) of the stream and display it on a monitor (114).

Figure 3:
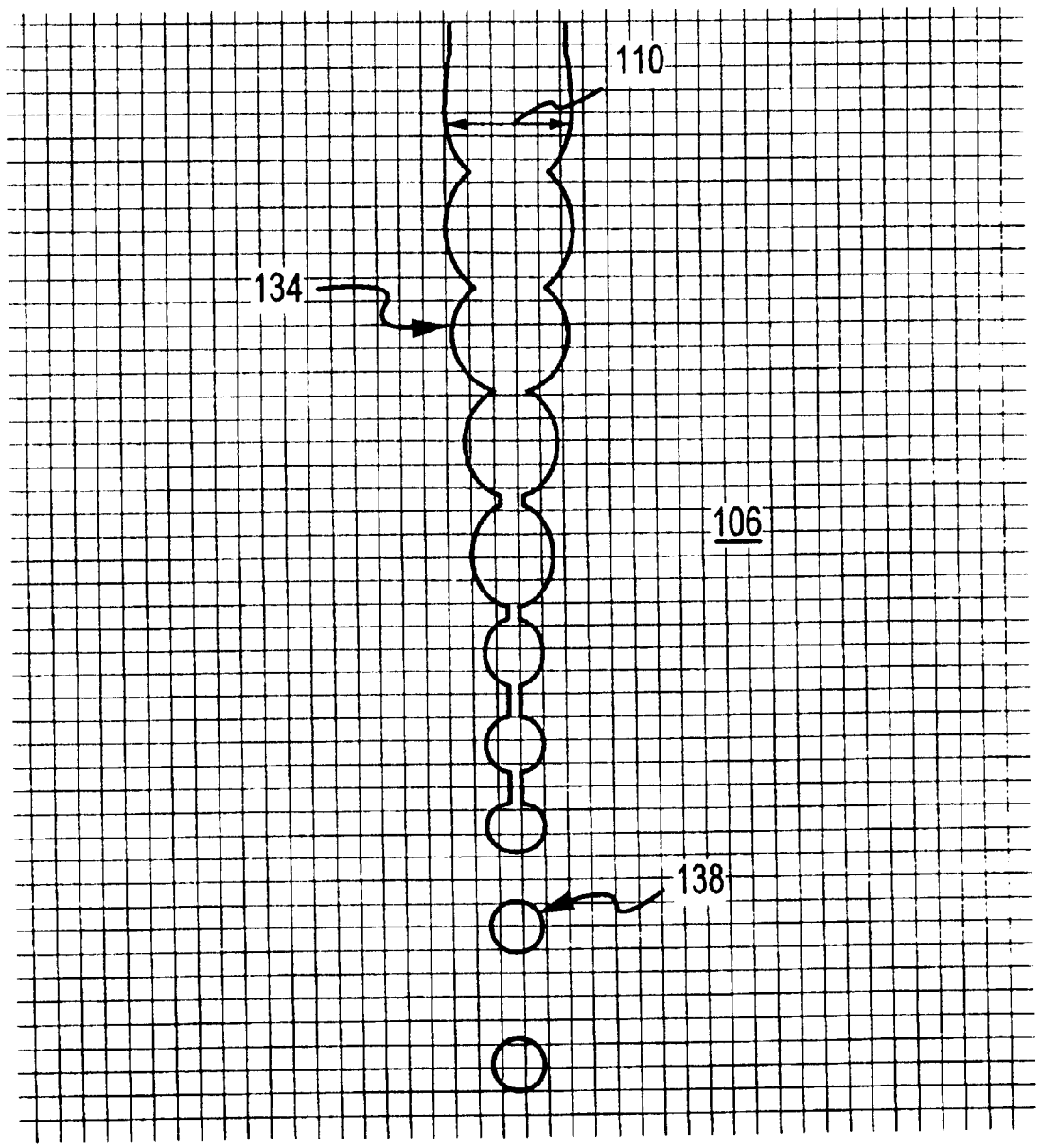
FIG. 3 is a view of a stream captured by a camera and displayed on a monitor with a pixel-based display.

The camera (102) can be oriented to capture various features of the stream. For example, the camera can be oriented to capture the width (110) of the stream as shown in FIG. 3. Alternatively or additionally, the camera can be oriented to capture an image that permits determination of a speed of the stream. As discussed earlier, this may be accomplished by measuring the wavelength of the stream or measuring a distance between two droplets and utilizing the known oscillation frequency to calculate a speed for the stream at those two points. Namely, the product of the oscillation frequency and the distance between droplets (or the stream wavelength) would yield a stream velocity at that point.

In addition, the camera or sensor may be oriented to capture an image that permits determination of a change in stream position. This can be done by monitoring a first position of the stream, recording that position, and then monitoring the stream over time to see if the stream moves away from that previously determined position. The camera can capture an image of the stream at the break-off point as well as the stream exit point where the stream emerges from the cytometer. Essentially, the camera can be oriented in many different orientations to capture many views in order to determine information about the stream which consequently allows the sensor to determine information about the characteristics of the cytometer. The various cameras can be used to capture the image of the stream, however it is preferred to use a camera that creates a digital representation for the image of the stream and one such camera being one that uses a charge coupled device or CCD. A CCD can produce an output in a series of analog voltage pulses each of which corresponds to a light intensity received by a pixel of the CCD.

Once the sensor (88) captures an image of the stream, the image can be displayed on a monitor (114). The monitor can then display the image of the stream to a user. Typically, a monitor (114) will also be comprised of individual pixel elements (118) that correlate to a digital embodiment of the image derived from the CCD. The CCD's pixel elements, as well as the monitor's embodiment) can be correlated with a physical distance to arrive at an accurate determination of an actual dimension of the stream. The monitor (114) can be positioned at the flow cytometer, or when it is desired to monitor the flow cytometer at a remote position, the monitor (114) can be positioned at such a remote position.

A memory device (122) can be used to store at least one parameter for the flow cytometer. Once an image is captured by the camera (102), the memory device can also serve to store a representation of the stream, more particularly, a digital representation of the stream. An imaging means (126) can be used by the sensor for creating a digital representation of the stream. More particularly, a means for outlining (130) can be utilized to create an outline of the stream (134) as shown in the representation of the stream in FIG. 3. Similarly, this means for outlining (130) can be used to create an outline of an individual droplet (138). Digital representation is intended to mean a representation of the object. For purposes of this patent it will still be considered a representation when only a portion or an outline of the border is used rather than the entire object. The means for outlining can be comprised of a typical digital imaging processing program or digital video processor which can operate on an image to detect actual signal versus noise in the signal. Such digital imaging processing programs can be seen by reference to: *Digital Imaging Processing* by Kenneth R. Castleman, Prentice Hall Dec. 1, 1995; *The Image Processing Handbook*, by John C. Russ, CRC Pr. January, 1995; *Digital Image Processing*, by Rafael C. Gonzalez, Addison-Wesley Apr. 1, 1992; and *Algorithms for Image Processing*, by James R. Parker, John Wiley & Sons Nov. 1, 1996 which are hereby incorporated by reference. Furthermore, U.S. Pat. No. 5,700,692 discusses imaging techniques and is hereby incorporated by reference for the imaging techniques disclosed.

An analyzer (142) can be used to analyze an image of the stream in order to determine information about the flow cytometer. For example, the analyzer can determine a distance between objects. Furthermore, the analyzer can determine a deflection of a charged droplet from the central axis of the stream based on the droplet position in the image and the uncharged stream steady state position. This can be accomplished by simply measuring the distance of the droplet from the steady state stream with a typical digital imaging processing program.

The analyzer (142) can also determine a charge on the droplet. For example, when one wants to know whether the proper charge was applied to a droplet the analyzer can be used to determine the actual charge as compared to the anticipated charge on the droplet. This can be accomplished by noting the deflection of the charged droplet from the stream noting the droplet size based on the image, measuring the mass of the droplet, which is a function of the droplet size and mass of the known fluid, and the known electric field set up by the deflection plates. In this fashion, the actual deflection can be used to deduce the charge on the droplet and therefore that actual charge can then be compared to the anticipated charge to confirm whether the charging procedure is actually charging the droplets to the proper charge. In addition, a droplet sizes can be detected at the breakoff point and the charging point adjusted to charge the droplets such that they will be deflected the appropriate distance given their size.

The analyzer can also be used to calculate the best "defanning" charge based on the deflection (or charge) of a previous droplet. For example, when one wants to establish a very steady stream of uncharged droplets, i.e., avoid a stream of uncharged droplets that make the stream appear like it is fanning back and forth, it is often necessary to apply a partial charge to droplets neighboring charged droplets. This is due to the fact that the charged droplets will induce a charge on neighboring droplets. Therefore, by slightly charging droplets that occur after a charged droplet, the induced charge on the successive droplets caused by the charged droplets can be counteracted. For example, if a positively charged droplet is expected to induce a negative charge on a successive droplet, the successive droplet can be charged slightly positive to counteract the induced effect.

The analyzer can also be used to measure the width of a stream which allows a determination of nozzle size. For example, the stream width of 60 microns (or 25 pixels on a 480×512 pixel image) can be determined to indicate a nozzle size of 70 microns. Furthermore, the analyzer can be used to determine the best resonant frequency for the cytometer. For example, the image can be analyzed to see where the stream establishes the shortest break-off point and the oscillation frequency of the oscillator can be set to correspond to that point. Typically, this will be a function of nozzle size and velocity.

Furthermore, the analyzer can be used to determine the speed of the stream based on distances determined in the image and the known frequency of the oscillator. To accomplish this analyzation process, the analyzer (142) can utilize a computer (146). The computer (146) can utilize the approximate speed of the stream at a first position and the approximate speed of the stream at a second position along the stream in order to determine a stream characteristic by modeling the speed of the stream in a region occurring between the stream exit point and the droplet break-off point as decaying approximately exponentially relative to distance.

Furthermore, the analyzer can utilize a means for determining a change in droplet break-off position (150) to determine when the break-off position of the stream changes.

This can be accomplished by recording a droplet break-off position and comparing that position to subsequent break-off positions noted in subsequent images. A simple computer program can be used to accomplish the means for determining a change in droplet breakoff position, by storing a representation of the droplet breakoff position, capturing a second digital representation and then comparing the two representations to see if they correspond.

The analyzer can also use a means for determining drop delay (154), the drop delay being associated with a detected particle. A drop delay (or drop delay time) is considered to be the delay in time between detecting a particle in the stream and acting upon the droplet in which the particle is contained in order to accomplish a sort of the particle. For example, in a typical flow cytometer, a particle will be detected by a detector and characteristics of the particle will be determined based on a fluorescence of light from the particle. Then, based on the characteristic, the droplet the particle is in will be charged just before it breaks away from the stream and sorted by an electrostatic sorter. The drop delay in this instance can be considered to be the time between detection of the particle and charging of the droplet. In another embodiment, one might choose to charge all the droplets, but only apply the electrostatic field for the particle/droplet to be sorted. In this case, the drop delay would be the time between the detection of the particle and the act of applying the electrostatic field. Similarly, the drop delay might be initiated at a point in time after the first detection of the particle, such as the time when the particle fluoresces. In this case, the drop delay might be calculated as the time between detection of a florescence and the time for the particle to reach the charging location. Similarly, for embodiments that use a charging ring to charge a droplet separate from the stream, the drop delay might be calculated from the point of particle detection to the point where charging occurs. Determination of the drop delay time can be accomplished with a simple software program for instance by determining a speed of the fluid stream at a particular position and modeling the speed of the stream based on an exponentially decaying speed with respect to distance. Therefore, the software routine could account for the change in speed of the stream over a distance and derive a time for the particle to traverse that distance to arrive at the charging location. For example, a comparator (158) can be used to compare determined information about the stream, for example, a measured property of the flow cytometer to a parameter of the flow cytometer. For purposes of this application, a parameter is a pre-determined or expected value for a characteristic of a thing, such as an expected width of a stream in a flow cytometer, an expected nozzle size, an expected break off position, an expected stream location, etc. On the other hand, and again for purposes of this application, a "property" is a quality, trait or quantitative value representative of a thing, such as the measured width of the flow cytometer stream, the measured pressure of the stream, the measured distance from a nozzle tip to the droplet break off point, the measured temperature of the stream, the actual mass of the fluid used for the stream, etc. The means for determining drop delay can utilize a compensator (162) to compensate for change in speed of the stream after the stream emerges at the exit point of the flow cytometer. Essentially this compensator can be comprised of a software routine that models the speed of the fluid as exponentially decaying, as those who are skilled in the art would easily understand.

A time delay generator (164) can be utilized by the flow cytometer (20) to provide a delay in charging the droplet which contains the detected particle once the particle is detected in the stream. Based on the results from an analyzer, the time delay generator can be set and used to control the droplet charger (84). A signal generator (168) can be used by the analyzer to generate a signal to the flow cytometer or to external indicators based on the determined information from the stream. For example, the signal generator can generate a signal used to re-establish the droplet break-off position. Furthermore, the signal generator can issue an error warning about the flow cytometer based on the determined information from the stream. In addition, the signal generator can be used to generate a signal to the flow cytometer based on the comparison of the first digital representation of the stream and a second digital representation of the stream as explained above.

FIG. 1 shows a remote paging device (172) that can be located with an operator of the flow cytometer when the operator leaves the area where the flow cytometer is located. Given the advancements of the present invention which allow the flow cytometer to detect catastrophic events, it is possible for an operator to leave the flow cytometer unattended and to perform activities elsewhere. The remote paging device can be used to warn the operator, for example, that a catastrophic event, i.e., an event which requires a cessation of sorting such as total loss of the stream, clogged tubes or nozzle, or air in the cytometer chamber, has occurred so that the operator can return to the flow cytometer and attend to whatever problem may exist. A remote computer monitor (176) can also be utilized with the flow cytometer to provide a similar warning. For example, the flow cytometer could be connected on a Windows NT platform such that a pop-up message can be displayed on an operator's terminal indicating the completion of a sort or a problem with the flow cytometer. Similarly, the flow cytometer can be connected to an E-mail system such that an E-mail message can be automatically routed to a user or interested party.

Alarm circuitry (180) can be utilized to indicate an alarm condition. Such circuitry may be comprised of an alarm (184) which can assume a variety of configurations such as a displayed message, a flashing light, a buzzer, or other commonly used devices.

Figure 4:
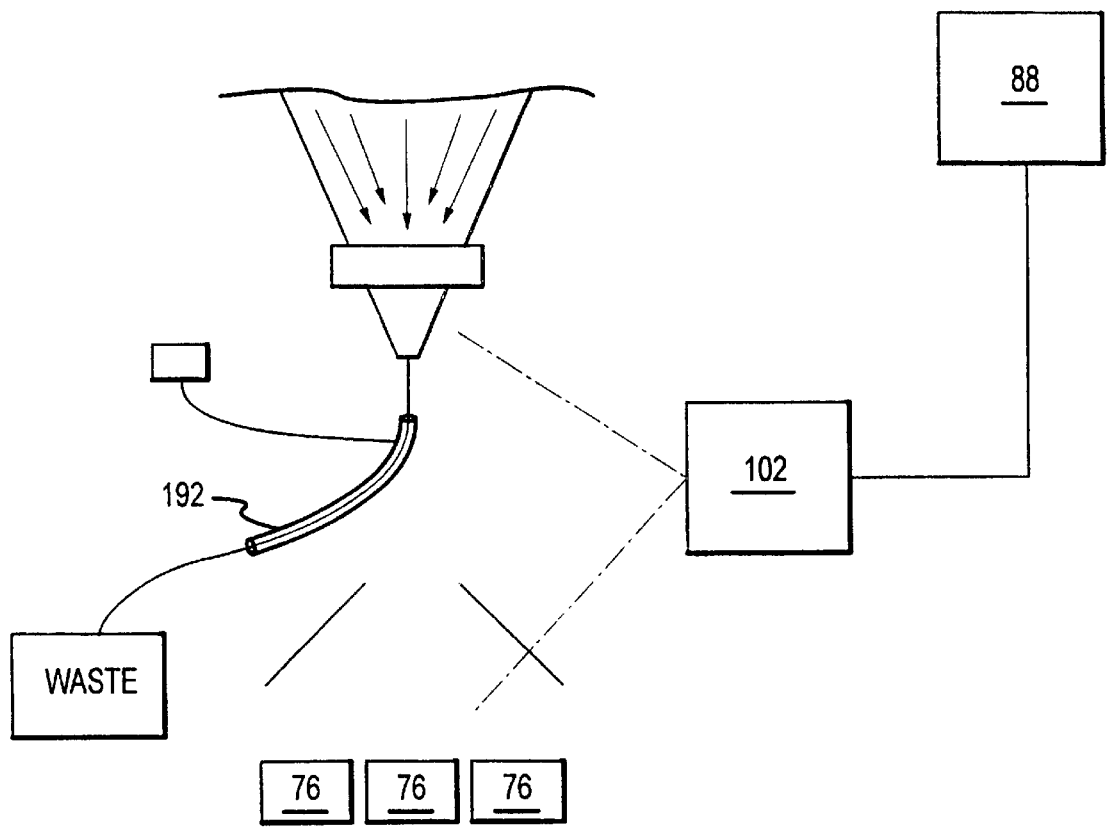
FIG. 4 is a first alternative of a flow cytometer with a mechanical interrupter.
Figure 5:
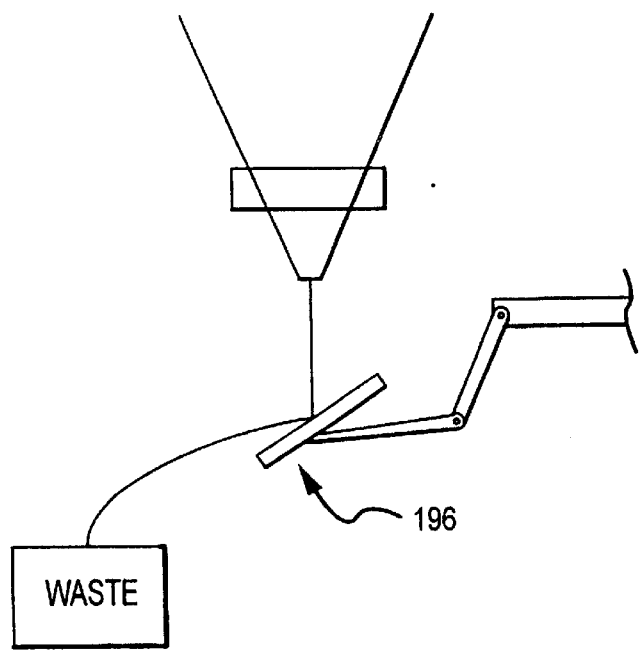
FIG. 5 is a second alternative of a mechanical interrupter for a flow cytometer.

One novel feature of a present embodiment of the invention is the use of a mechanical interrupter (188) which can be utilized to intercept and/or interrupt the stream. For example, the mechanical interrupter (188) may be utilized after the stream exits from the exit point of the flow cytometer such that the stream can be interrupted and diverted away or deflected away from its normal course or from the abnormal course that is caused due to a problem with the flow cytometer. The mechanical interrupter can be used to interrupt the stream based on a determination made by the sensor. In this fashion it can work automatically. One possible embodiment of the mechanical interrupter can utilize a gutter (192) as shown in FIG. 4 which routes the stream away to a waste container after the gutter swings in to intercept the stream. Alternatively, a deflector (196) can be used to swing into position such that the stream is deflected away to the waste container. Preferably these mechanical interrupters are located close to the exit point of the stream such that the stream can be diverted as early as possible to avoid contamination of the collected samples. Both may swing or slide in either manually or automatically.

With a background understanding of the apparatus of the present invention, the method of utilizing the apparatus to accomplish various embodiments of the invention can now be better understood. In particular, one aspect of the present invention involves utilizing an imaging system to capture images of the stream. Particularly the droplet break-off point of the stream can be captured as an image such that a speed of the stream can be determined. This can be accomplished by imaging the stream and identifying droplets that form below the droplet break-off point and determining a distance using imaging techniques between subsequent droplets. These droplets will be traveling at a speed very close to the droplet that is located at the droplet break-off point. The image of the stream can be stored as a digital image in memory, e.g., RAM, of the cytometer.

Imaging techniques can be utilized to analyze the stream. For example, electrical noise can be eliminated from a captured image. This may involve capturing a first image of the stream at a location along the stream and creating a first digital representation of the stream based on the first image. For example, an outline of the stream might be created. Then that digital representation of the stream can be stored in memory. For example, the outline can be stored in memory. Additionally, an outline of a droplet from the stream can be created and stored in memory as well. Next, a second image of the stream at the same location can be captured and a second digital representation created. The second digital representation of the stream can be based on the second captured image. Then, the two digital representations of the stream can be compared and a determination can be made whether a property of the stream has changed based on the comparison of the first digital representation with the second digital representation. Standard digital signal processing techniques can be used to accomplish this as would be understood by those of ordinary skill in the arts.

Furthermore, one embodiment of the invention can determine information about the flow cytometer based on a captured image. For example, this might be accomplished by measuring a property of the flow cytometer based on the captured image. Such properties might include the width of the stream, the speed of the stream, the pressure of the fluid, the wavelength of a wave on the stream indicative of the stream speed, or other characteristics. Furthermore, information can be determined about the flow cytometer by associating a physical distance with a digital image block or a pixel dimension. An actual physical distance can be determined based on the number of blocks or pixels used to represent that distance on the captured image.

The captured image can also be used to determine a velocity of the stream. This can be accomplished by measuring a wavelength of the stream at some position along the stream. Furthermore, the oscillation frequency of the oscillator can be used in conjunction with the measured wavelength to calculate an approximate speed of the stream. A velocity of the stream can be determined at an approximate exit point where the stream emerges from the flow cytometer by measuring a wave length there and utilizing the known oscillator frequency. In addition, an approximate velocity of the stream can be measured at about the droplet break-off point by imaging droplets and measuring the distance between successive droplets. By utilizing the oscillation frequency to determine the time period between successive droplets and given the measured distance an approximate velocity can be calculated for the droplet break-off point.

The captured image can also be utilized to determine a drop delay time for a particle in the stream. This can be accomplished by determining an approximate first speed of the stream at a location along the stream and then determining an approximate second speed of the stream at a different point along the stream. Preferably a speed close to the particle detection point would be utilized for the first speed of the stream and a measurement of the stream speed at approximately the droplet break-off point would be utilized for the second speed of the stream. These two speeds can then be used as part of a model for purposes of modeling the stream speed. Experimental results indicate that the speed of the stream will approximately exponentially decay from the point where it is ejected from the flow cytometer to a typical droplet break-off point. However, an appropriate function of the speed could easily be determined for a stream by generating calibration data for stream once the stream was established and deriving a real function for the change in speed of that stream for the actual conditions. A typical velocity of the stream at the exit point will typically, in one embodiment of the invention, approach 27 meters per second, while at the break-off point the velocity will have dropped to 25 meters per second. This is believed to be due to hydrodynamic relaxation of the stream over the distance from the exit point to the droplet break-off point. In previous attempts by others to determine an appropriate drop delay time those earlier attempts had utilized a constant velocity throughout this range of the stream. Therefore, this probably resulted in a less accurate drop delay time and consequently a poorer result in charging a desired droplet. Consequently, once the first speed of the stream and the second speed of the stream are measured, the stream speed can be modeled as decaying approximately exponentially—as experimental data suggest—in the region between the exit point and the droplet break-off point. Then, given the point where a particle is detected and a known distance to a charging point for the droplet containing the particle (or even by determining that distance through imaging of the stream by determining the present droplet break-off point when the particle was detected or monitoring a shift in that droplet break-off point as the particle descends in the stream), the flow cytometer can compensate for the change in speed due to the exponential decay of the speed of the stream in the region. Then based on this modeling of the stream speed and the compensation for the change in speed the flow cytometer can determine a time for the particle to flow over the distance to the charging point. In this fashion, the approximate speed of the stream at the first position along the stream and the approximate speed of the stream at the second position along the stream can be used to determine the stream characteristic, namely in this example, a drop delay time for the stream.

Once a drop delay time has been calculated that drop delay time can be utilized to calculate when the particle will reach a droplet charging location, e.g., based on the known point in time when the particle was detected. Then, the flow cytometer can charge the droplet containing the particle as it reaches the charging location, for example, by charging the stream or by using a charging ring.

As noted earlier, a present embodiment of the invention can be used to measure properties about the flow cytometer in order the generate warnings about the flow cytometer. This can involve defining at least one parameter for the flow cytometer and comparing that parameter to a measured property or characteristic of the flow cytometer. In view of this comparison the flow cytometer can then determine when the operation of the flow cytometer does not satisfy at least one parameter defined for the flow cytometer.

For example, a warning can be generated after determining that a change in position of the droplet break-off point has occurred. In previous setups, others have relied on a technician to constantly watch an image of the stream to see if the droplet break-off point shifts in position. With the present imaging techniques that allow comparison of previous droplet break-off points with successive droplet break-off points, this procedure can be automated such that a warning signal is generated to an operator of the flow cytometer.

As another example, the flow cytometer allows for adjusting a drop delay time so as to properly charge a droplet at the droplet break-off point. This can involve detecting the speed of the stream and the current known droplet break-off point at the point in time when the particle is detected, and then calculating the drop delay time for that particular particle or even adjusting that drop delay time again as a droplet break-off point change is sensed after particle detection.

Furthermore, a present embodiment of the invention is to constantly monitor and re-establish the position of the droplet break-off point (or fiducial break-off point) (48) from the stream. The instant invention allows the determination of the position of the droplet break-off point to be ascertained relative to the fixed point of detection of the particle in the stream by the particle detection system or detector, or laser and receiver (72). This assessment of the position may be accomplished by taking sequential high resolution scans or images with a camera or monitor (102) synchronized with the strobe phase and the droplet charging phase (84) so as to record an image of sequential droplets as they reach the break-off point from the stream. The images of the droplets at the location of break-off is digitized(126) and held in a memory device (122). Digitized data relating to the location of the droplet break-off points is then compared electronically. The distance between droplet break-off points may be determined by the digital image processing program. Then, as the droplet break-off point begins to shift in either direction, a feedback signal may be generated to either increase or decrease the amplitude of the oscillations from the oscillator (68) in order to re-establish the droplet break-off point in its previous position. The position of the droplet break-off point may be re-established in this manner because the distance at which droplet break-off occurs from a stream is a function of the stream velocity (Vb), the disturbance amplitude, and a time constant which is a function of surface tension, fluid density, jet diameter $(d_j)_j$ and wavelength. The disturbance amplitude (Va) is proportional to the oscillator voltage to the oscillator (68) through a coupling constant (Cc). Therefore, droplet break-off distance (Xb) which varies relative to a fixed position due to fluctuation in stream velocity, may be held constant by varying the disturbance amplitude while wavelength, fluid density, surface tension and jet diameter are held constant. These relationships are summed up in the following equation:

$$Xb = Vb.Te(Vb,d) - Vb.\log(Cc.Va)/\gamma$$

where Te is a delay correction due to the non-uniform velocity profile of the stream where Te=k/Vb=332.0/Vb, and γ is defined by a Rayleigh analysis where $$\gamma = \sqrt{\{(8 \cdot \sigma/(\rho \cdot d_j^3)(\xi \cdot (1-\xi)I_1(\xi)/I_0(\xi)\}},$$

and where $\xi = \pi.d_j.f/Vb$, as such using standard Rayleigh parameters.

These functional relationships are used in conjunction with computer software and computer hardware to create a oscillation control device which generates a signal which adjusts the voltage to the oscillator which varies the oscillations to the stream in response to the variation in location of the fiducial break-off point. The variation of oscillation to the stream thereby maintains the location of the fiducial break-off point. Failure to maintain the fiducial break-off point may lead to a computer controlled automatic suspension of sorting activity.

In another embodiment of the invention an alarm or warning based on the information in or determined from the captured image can be generated. Such an alarm or warning can be based on a comparison of the determined information about the flow cytometer with an expected characteristic of the flow cytometer. This might involve issuing an error warning about the flow cytometer based on a comparison of the determined information and the expected characteristic.

The types of warnings that can be issued by the flow cytometer can be seen through the following examples. For example, it might be desirable to compare an expected stream width, such as stream width (110) shown in FIG. 3 with a predetermined stream width expected for use in a particular set-up or for a particular particle to be sorted. In this fashion if an expected stream width is expected and a different stream width is measured, a warning can be generated to the user or operator indicating that an incorrect nozzle size may be connected to the flow cytometer. Similarly, the error warning might indicate that an improper pressure is being used. In addition, as noted earlier, the imaging technique can be utilized to determine a speed of the stream and this determination of the stream speed might be utilized to issue a warning about the pressure of the stream. If an expected stream pressure would create a predetermined stream speed and a measured stream speed were different from that predetermined stream speed, then an error warning might be appropriate. One significant aspect of the present invention is its ability to react to a catastrophic failure of the cytometer. This might be most noticeable through a significant change in position of the stream due to clogging of the nozzle. The imaging of the stream would allow a steady state position of the stream to be recorded and compared to subsequent images of the stream. When a clogged nozzle, for example, diverts the stream at an angle, the imaging technique of comparing subsequent images to a steady state image would allow the flow cytometer to determine that a catastrophic event was occurring and issue a warning to the user or even automatically interrupt the sorting process in order to perfect the previously sorted sample. The warning can be generated in a variety of ways. One such way might be through displaying a warning on a remote computer monitor where an operator is working. Furthermore, a warning might be issued to a paging device.

Another significant embodiment of the invention allows the flow cytometer to disable the source based on information determined from a captured image. For example, given the catastrophic failure detected earlier due to a diversion of the stream or even the complete loss of stream, the flow cytometer can act by mechanically interrupting the sort. This can be accomplished by automatically moving, swinging, or sliding a gutter as shown in FIG. 4 so as to intercept the stream and then channeling away the stream in the gutter to a waste receptacle. Alternatively, this mechanical interruption might be caused by automatically moving, sliding, or swinging a deflector, for example, a plate, in order to deflect the stream away from the collected sample that was already produced by the flow cytometer. Alternatively, or perhaps even in addition to, where the stream is still present, the flow cytometer can automatically act to turn off the charging device or the deflection source such that the charged particles are not deflected into the collected sample.

Finally, one embodiment of the invention can be utilized to automatically issue an alarm signal. In this fashion an operator can be notified that the flow cytometer has an alarm condition, for example, any abnormal condition. Such alarm signals might utilize either an audible or visual alarm.

The foregoing discussion and the claims that follow describe the preferred embodiments of the present invention. Particularly with respect to the claims it should be understood that changes may be made without departing from the essence of the invention. In this regard, it is intended that such changes would still fall within the scope of the present invention. It is simply not practical to describe and claim all possible revisions which may be accomplished. To the extent such revisions utilize the essence of the present invention, each naturally falls within the breadth of protection encompassed by this patent. Further, it should be understood that various permutations and combinations of the elements shown in the claims are possible and should fall within the scope of this disclosure. In addition, it should be understood that the use of the word "comprising" is intended to have an inclusive meaning rather than an exclusive meaning. Therefore, in foreign countries, such as Australia, where this application may be relied upon as a priority document, the meaning of the word "comprising" is intended to have an inclusive meaning.

The discussion included in this application is intended to serve as a basic description. The reader should be aware that the specific discussion may not explicitly describe all embodiments possible; many alternatives are implicit. The market place and manufacturing concerns may dictate the appropriate embodiments for the present invention. Particularly with respect to the discussion, it should be understood that a number of changes may be made without departing from the essence of the present invention. In this regard, it is intended that such changes—to the extent that they substantially achieve the same results in substantially the same way—will still fall within the scope of the present invention. It also may not fully explain the generic nature of the invention and may not explicitly show how each feature or element can actually be representative of a broader function or of a great variety of alternative or equivalent elements. Again, these are implicitly included in this disclosure. Where the invention is described in apparatus-oriented terminology, each element of the apparatus implicitly performs a function. Apparatus discussions or claims may not only be included for the systems described, but also method or process claims may be included to address the functions the invention and each element performs. As but one example of this aspect, the disclosure of a "sensor" should be understood to encompass disclosure of the act of "sensing"—whether explicitly discussed or not—and, conversely, were there only disclosure of the act of "sensing", such a disclosure should be understood to encompass disclosure of a "sensor." Although the methods related to the system are being included in various detail, only an initial discussion directed toward the biosensor has been included. Naturally, that discussion could have some application to the various other methods and aspects discussed throughout the disclosure. Neither the description nor the terminology is intended to limit the scope of the claims which will be included in a full patent application.

What is claimed is:

1. A method of flow cytometry comprising:
   establishing a stream which emerges from a nozzle at a stream exit point, wherein the stream has a droplet break off point at which droplets break off and a free fall zone in which the droplets fall;
   determining an approximate speed of the stream at a first position along the stream;
   determining an approximate speed of the stream at a second position along the stream; and
   modeling the speed of the stream as decaying approximately exponentially relative to distance in a region occurring between about the stream exit point and about the droplet break off point.

2. The method of flow cytometry as described in claim 1 further comprising the step of utilizing the approximate speed of the stream at the first position along the stream and the approximate speed of the stream at the second position along the stream to determine a stream characteristic.

3. The method of flow cytometry as described in claim 1 further comprising the steps of:
   measuring a wavelength of the stream;
   utilizing an oscillation frequency of an oscillator of the flow cytometer; and
   calculating an approximate speed of the stream at a measured wavelength position based on the measure of the wavelength and the oscillation frequency.

4. The method of flow cytometry as described in claim 3 wherein the step of measuring a wavelength of the stream comprises measuring a wavelength of the stream at about the exit point of the flow cytometer.

5. The method of flow cytometry as described in claim 1 or 4 further comprising the steps of:
   measuring a distance between droplets of the stream;
   utilizing an oscillation frequency of an oscillator of the flow cytometer; and
   calculating an approximate speed of the stream based on the measured distance between droplets and the oscillation frequency.

6. The method of flow cytometry as described in claim 3 wherein the step of measuring a wavelength of the stream comprises measuring a wavelength of the stream at about the droplet break off point.

7. The method of flow cytometry as described in claim 1 or 4 further comprising the steps of:
   detecting a particle in the stream;
   determining a point in time when the droplet in which the particle is located will break off from the stream; and
   charging the stream so that the droplet containing the particle is charged.

8. A flow cytometer comprising:
   a source of stream fluid to establish a stream;
   a stream exit point where the stream is emerges from the flow cytometer;
   a droplet break off point where the stream breaks off into droplets;

a first sensor to determine an approximate speed of the stream at a first position along the stream;

a second sensor to determine an approximate speed of the stream at a second position along the stream; and a computer to utilize the approximate speed of the stream at a first position along the stream and the approximate speed of the stream at a second position along the stream in order to determine a stream characteristic by modeling the speed of the stream in a region occurring between the stream exit point and the droplet break off point as decaying approximately exponentially relative to distance.

9. The flow cytometer as described in claim 8 further comprising:

a sensor oriented to measure a wavelength of the stream; and an oscillator having an oscillation frequency to perturb the stream to generate droplets.

10. The flow cytometer as described in claim 8 further comprising a sensor oriented to measure a wavelength of the stream at about the stream exit point of the flow cytometer.

11. The flow cytometer as described in claim 8 or 10 further comprising a sensor oriented to determine a distance between droplets below the droplet break off point.

12. The flow cytometer as described in claim 8 or 10 further comprising a sensor oriented to measure a wavelength of the stream at about the droplet break off point.

13. A method of flow cytometry comprising:

establishing a stream comprising a flow of particles, the stream having a droplet break off point;

creating a first droplet, the first droplet having an electrical charge;

capturing an image of the stream;

creating a second droplet in proximity to the first droplet;

determining an effect that the electrical charge on the first droplet will have on the second droplet;

generating a signal for the flow cytometer based on the determined effect; and charging the second droplet to counteract the determined effect that the charge on the first droplet will have on the second droplet.

14. A method of controlling a flow cytometer, comprising the steps of:

establishing a stream comprising a flow of particles, the stream having a droplet break off point;

capturing an digital image of the stream to determine a drop delay time for a particle in the stream; and generating a signal for the flow cytometer, wherein a time of generation of the signal is adjusted based on the determined drop delay time from the captured image.

15. The method of controlling a flow cytometer as described in claim 14 and further comprising the step of using a CCD camera to capture the image.

16. The method of controlling a flow cytometer as described in claim 14 and further comprising the steps of:

associating a physical distance with a pixel dimension; and determining a physical distance based on the number of pixels used to represent that distance in the captured image.

17. The method of controlling a flow cytometer as described in claim 14 further comprising the step of determining a speed of the stream at about an exit point, wherein the exit point is located where the stream emerges from the flow cytometer.

18. The method of controlling a flow cytometer as described in claim 14 or 17 further comprising the step of determining a speed of the stream at about the droplet break off point.

19. The method of controlling a flow cytometer as described in claim 14 further comprising the steps of:

determining a speed of the stream at about an exit point, wherein the exit point is located where the stream emerges from the flow cytometer; and determining a speed of the stream at about the droplet break off point.

20. The method of controlling a flow cytometer as described in claim 14 further comprising the steps of:

detecting a particle;

utilizing the drop delay time to calculate when the particle in a droplet will reach a droplet charging location; and charging the droplet containing the particle at the charging location.

21. The method of controlling a flow cytometer as described in claim 14 or 20 further comprising the steps of:

determining a first speed of the stream;

determining a second speed of the stream; and utilizing the first speed of the stream and the second speed of the stream to model a change in speed of the stream in order to determine the drop delay time.

22. The method of controlling a flow cytometer as described in claim 14 further comprising the step of determining a change in position of the droplet break off point.

23. The method of controlling a flow cytometer as described in claim 22 further comprising the step of compensating for the change in the droplet break off point so as to sort a droplet in a desired fashion.

24. The method of controlling flow cytometer as described in claim 22 further comprising the steps of:

generating a signal to adjust the flow cytometer; and reestablishing the droplet break off point based on the generated signal.

25. The method of controlling a flow cytometer as described in claim 14 further comprising the step of eliminating electrical noise from the captured image.

26. A flow cytometer comprising:

a source of stream fluid;

a source of particles for suspension in the stream fluid;

a stream comprising the stream fluid and the particles;

a nozzle through which the stream is established;

a break off point of the stream at which point the stream breaks off into droplets, said droplets centered about the break off point;

a camera that captures an image of the stream;

an analyzer that analyzes the image of the stream to determine the effect that a first charged droplet has on a second droplet; and a signal generator to generate a signal based on the determined effect that the first charged droplet has on the second droplet.

27. A flow cytometer comprising:

a source of stream fluid;

a source of particles for suspension in the stream fluid;

a stream comprising the stream fluid and the particles;

a nozzle through which the stream is established;

an exit point at which said stream emerges from said nozzle;

a break off point of the stream at which point the stream breaks off into droplets, said droplets centered about the break off point;

a camera that captures a digital image of the stream;

an analyzer that analyzes the digital image of the stream to determine a drop delay time for a particle in the stream; and a signal generator to generate a signal, for the flow cytometer wherein a time of generation of the signal is adjusted based on the determined drop delay time.

28. The flow cytometer apparatus as described in claim 27 wherein the camera comprises a Charge Coupled Device.

29. The flow cytometer apparatus as described in claim 27 and further comprising a monitor to display the stream, wherein the monitor is comprised of pixels.

30. The flow cytometer as described in claim 27 further comprising a sensor to measure a speed of the stream at about the exit point of the stream.

31. The flow cytometer as described in claim 27 or 30 further comprising a sensor to measure a speed of the stream at about the droplet break off point.

32. The flow cytometer as described in claim 27 further comprising:

a sensor to measure a speed of the stream at about the exit point of the stream; and a sensor to measure a speed of the stream at about the droplet break off point.

33. The flow cytometer as described in claim 27 further comprising a time delay to be used in delaying a droplet charger after a particle is detected in the stream.

34. The flow cytometer as described in claim 33 further comprising a compensator to compensate for a change in speed of the stream of the flow cytometer after the stream emerges at the exit point of the flow cytometer.

35. The flow cytometer as described in claim 27 further comprising a means for determining a change in the droplet break off position.

36. The flow cytometer as described in claim 35 further comprising a compensator to compensate for a change in speed of the stream of the flow cytometer after the stream emerges at the exit point of the flow cytometer.

37. The flow cytometer as described in claim 35 further comprising a signal generator to generate a signal used to reestablish the droplet break off position.

38. The flow cytometer as described in claim 27 further comprising an alarm to indicate an alarm condition.

39. The flow cytometer as described in claim 27 further comprising a mechanical interrupter to intercept the stream after the stream exits at the exit point of the flow cytometer.

40. A method comprising:

establishing a stream in a flow cytometer;

capturing a first image of the stream established in the flow cytometer;

creating a first digital representation of the stream based on the first image;

capturing a second image of the stream established in the flow cytometer;

creating a second digital representation of the stream based on the second image;

comparing the second digital representation of the stream to the first digital representation of the stream; and determining whether a property of the stream has changed based on the comparison of the first digital representation of the stream with the second digital representation of the stream.

41. The method as described in claim 40 further comprising the step of creating an outline of the stream.

42. The method as described in claim 41 wherein the act of creating an outline of the stream further comprises creating an outline of a droplet.

43. The method as described in claim 41 or 22 further comprising the step of storing an outline of the stream in memory.

44. The method as described in claim 40, 41, or 42 and further comprising the steps of:

comparing the second digital representation to the first digital representation; and detecting a change in the representation of the stream between the first digital representation and the second digital representation.

45. A flow cytometer apparatus comprising:

a stream source used to establish a stream;

a camera to capture images of the stream;

an imaging means for creating digital representations of the stream;

a memory to store a first digital representation of the stream;

a comparator to compare the first digital representation of the stream with a second digital representation of the stream; and a signal generator to generate a signal to the flow cytometer based on the comparison of the first digital representation of the stream with the second digital representation of the stream.

46. The flow cytometer as described in claim 45 further comprising a means for outlining to create an outline of the stream.

47. The flow cytometer as described in claim 46 wherein the outlining means is configured to create an outline of a droplet.

* * * * *